Oct. 20, 1964 R. S. MOORE Plant Pat. 2,450

MINIATURE ROSE PLANT

Filed June 12, 1963

WITNESS

Jeanette Nunn Copley

INVENTOR

Ralph S. Moore

Webster & Webster

ATTYS.

United States Patent Office

Plant Pat. 2,450
Patented Oct. 20, 1964

2,450
MINIATURE ROSE PLANT

Ralph S. Moore, 2519 E. Mineral King, Visalia, Calif.

Filed June 12, 1963, Ser. No. 287,452
1 Claim. (Cl. Plt.—8)

Figures 1, 2:
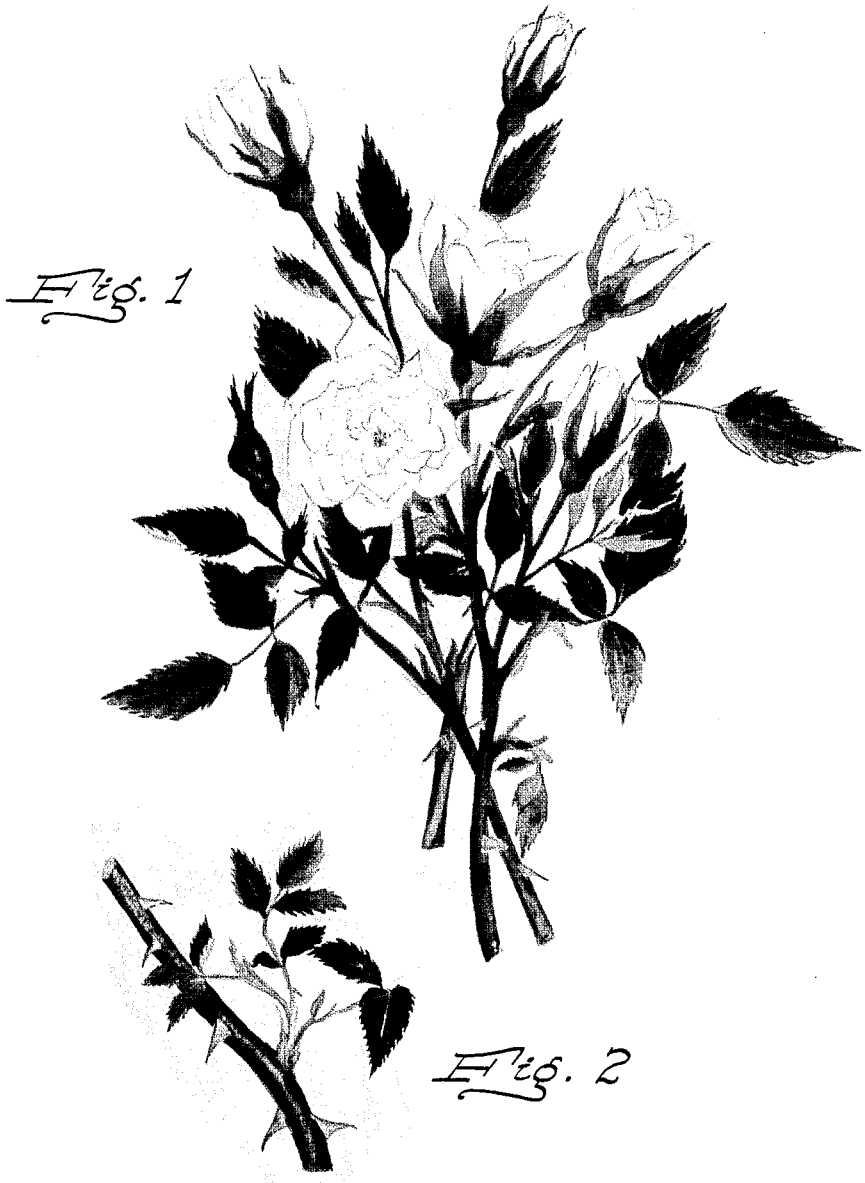

This invention relates to a new and distinct variety of hardy, dwarf, bush type of rose plant of the hybrid miniature class.

The present variety of miniature rose plant was originated by me in my nursery located at Visalia, County of Tulare, California, under conditions of careful control and observation, as a seeding which resulted from a cross between Golden Glow (United States Plant Patent No. 263) as the seed parent and Zee (an unpatented miniature) as the pollen parent.

Subsequent to the origination of the variety and recognition by me of its distinctive features as hereinafter described, I successfully asexually reproduced it in my nursery, located as aforesaid, by budding as well as by cuttings; such asexual reproductions having run true to the original plant in all respects.

In plant habit and shape of flowers, the present variety is generally similar to Easter Morning (United States Plant Patent No. 2,177) but is distinctively characterized as follows:

The variety is the easiest of all yellow flowered miniature roses to propagate and to grow into a saleable plant; this by reason of a very definite ease of rooting from both hard and soft wood cuttings, and a high percentage of survival of newly potted rooted cuttings.

The plant, while vigorous in growth, is quite compact and has an abundance of glossy clean foliage; the plant growing well both outside and in a greenhouse.

The variety is a regular or continuous bearer of double, many petaled flowers having a tea rose fragrance and being clear yellow in color; the buds being well shaped (much like a hybrid tea rose) while the old flowers shed their petals so that the plant is clean and neat in appearance at all times.

The flowers, while remaining a clear yellow, may vary in shade due to light intensity or day length. When the plants are grown in a greenhouse with the use of artificial light to provide in effect an increase in day length, full colored buds and flowers can be produced even during the winter months.

In the drawings, FIG. 1 illustrates a spray, including foliage, buds and flowers, and FIG. 2 illustrates a section of a stem, with thorns and a leaf.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bush; seeding; greenhouse; outdoors; cut flowers; garden decoration.

Class: Hybrid miniature.

Flowers:

*Continuity.*—Intermittent, continuous.

*Fragrance.*—Moderate; tea rose.

Flowers borne: Singly, or 2 or 3 in irregular clusters on normal strength medium length stems.

Quality of bloom: Free and abundant, both outdoors and in greenhouse.

Bud:

*Peduncle.*—Short to medium length; medium strength; erect. Medium Green, 860/1. Smooth; numerous fine short green hairs.

*Before calyx breaks.*—Size—small. Form—pointed; oval; with some foliaceous appendages on the surface of the bud; with slender foliaceous parts extending beyond the tip of the bud equal to one-fourth to one-half of its length. Color—Medium Green, 860/1.

*As calyx breaks.*—Color—yellow.

*As first petal opens.*—Size—small. Form—pointed; ovoid. Color: outside—yellow, between Aureolin, 3/1 and Canary Yellow, 2/2; inside—yellow, between Aureolin, 3/1 and Canary Yellow, 2/2.

*Opening.*—Opens well in all weather.

Bloom:

*Size when fully open.*—Small, averaging 1½" to 2".

*Petalage.*—Very double, with from 60 to 75 or more petals arranged regularly.

*Form.*—Flat and full at first; petals remaining at first loosely rolled outward and later at maturity being flat cupped and loosely rolled outward.

Petals:

*Thickness.*—Medium.

*Texture.*—Satiny, both inside and outside.

*Shape.*—Outside—ovate. Intermediate—ovate. Inside—lanceolate.

*Color.*—Newly opened flower from plant grown in greenhouse (May 1963), Visalia, California—Outside petal: outside surface—Canary Yellow, 2/2 shading to Canary Yellow, 2/1 at base; inside surface—Aureolin, 3/2 shading to Canary Yellow, 2/1 at base. Intermediate petal: outside surface—Canary Yellow, 2/2 shading to Canary Yellow, 2/1 at base; inside surface—Aureolin, 3/2 shading to Canary Yellow, 2/1 at base. Inner petal: outside surface—Canary Yellow, 2/2 shading to Canary Yellow, 2/1 at base; inside surface—Canary Yellow, 2/2 shading to Canary Yellow, 2/1 at base. A flower that was open for three days in a greenhouse (May 1963), Visalia, California—Outside petal: outside surface—Canary Yellow, 2/3 shading to Canary Yellow, 2/2 at base; inside surface—Canary Yellow, 2/3 shading to Canary Yellow, 2/2 at base. Inside petal: outside surface—Canary Yellow, 2/3 shading to Canary Yellow, 2/2 at base; inside surface—Canary Yellow, 2/3 shading to Canary Yellow, 2/2 at base.

*General color effect.*—Newly opened flower—Canary Yellow, 2/3 shading to Canary Yellow 2/2 at base. Three days open—Canary Yellow, 2/3 shading to Canary Yellow, 2/2 at base.

*Behavior.*—Best color in warmer weather with extended day length and ample light as in summer. Cool fall and spring weather with shorter day length may cause lighter color, although buds and flowers remain of good form. Petals drop off cleanly.

*Flower longevity (May 1963).*—Bush in garden—four to five days. Cut flowers kept at living room temperature—two to three days.

Reproductive Organs:

*Stamens.*—Few; arranged irregularly about pistils; mixed with petaloids.

*Filaments.*—Short; yellow; most without anthers.

*Anthers.*—Small; yellow.

*Pollen.*—Sparse to none; yellow.

*Pistils.*—Medium number.

*Styles.*—Uneven; short to medium length; thin; loosely bunched.

*Stigma.*—Yellow.

*Ovaries.*—All enclosed in calyx.

*Hips.*—None.

*Sepals.*—Falling soon; spear shaped; recurved; green.

*Seeds.*—None.

*Plant*

Foliage:

*Leaves.*—Compound of five to seven leaflets; abundant; moderately small; moderately heavy; glossy.

*Leaflets.*—Shape—lanceolate. Apex—acute. Base—round. Margin—serrate.

*Color.*—Upper surface—Medium Green, o960. Under surface—Lighter Gray-Green, ooo761.

*Rachis.*—Medium strength. Upper side—grooved, with a few tiny hairs or prickles. Under side—sparsely thorny, 2 to 4.

*Stipules.*—Moderately long. Narrow, with medium long points turning out at an angle of more than 45 degrees.

Growth:

*Habit.*—Dwarf; bushy; much branched.

*Growth.*—Free.

*Canes.*—Medium strength.

*Main stems.*—Color—Green. Thorns—several; medium length; straight or hooked slightly downward, with narrow base. Pricles—none to few. Hairs—none.

*Branches.*—Color—bright green. Thorns—several; medium length; hooked slightly downward. Prickles—none. Hairs—none.

*New shoots.*—Color—bright green. Thorns—few to several; nearly straight. Prickles—none. Hairs—none.

The miniature rose plant and its flowers as herein described may vary in slight detail due to climatic and soil conditions under which the variety may be grown; the present description being of the variety as grown at Visalia, California.

The following is claimed:

A new and distinct variety of miniature rose plant of hardy, dwarf, bush type, substantially as illustrated and described, having general similarity to Easter Morning in plant habit and shape of flowers but distinctively characterized by ease of propagation from hard or soft wood cuttings, and a high percentage of survival of newly potted rooted cuttings; by a vigorous, compact, but much branched plant having an abundance of clean glossy foliage, the plants growing well both outdoors and in a greenhouse; by buds which are well shaped and resemble a hybrid tea rose; and by double, many petaled flowers having tea rose fragrance and clear yellow color, which flowers when old shed their petals.

No references cited.